(12) United States Patent
Lim

(10) Patent No.: US 9,414,910 B2
(45) Date of Patent: Aug. 16, 2016

(54) ANCHORING DEVICE FOR A PROSTHETIC HEART VALVE

(71) Applicant: ASSISTANCE PUBLIQUE—HOPITAUX DE PARIS, Paris (FR)

(72) Inventor: Pascal Lim, Paris (FR)

(73) Assignee: ASSISTANCE PUBLIQUE—HOPITAUX DE PARIS, Paris (FR)

( * ) Notice: Subject to any disclaimer, the term of this patent is extended or adjusted under 35 U.S.C. 154(b) by 0 days.

(21) Appl. No.: 14/371,801

(22) PCT Filed: Jan. 10, 2013

(86) PCT No.: PCT/EP2013/050412
§ 371 (c)(1),
(2) Date: Jul. 11, 2014

(87) PCT Pub. No.: WO2013/104721
PCT Pub. Date: Jul. 18, 2013

(65) Prior Publication Data
US 2015/0045881 A1  Feb. 12, 2015

(30) Foreign Application Priority Data
Jan. 13, 2012  (FR) ...................................... 12 50357

(51) Int. Cl.
*A61F 2/24* (2006.01)
*A61L 27/04* (2006.01)
*A61L 27/34* (2006.01)

(52) U.S. Cl.
CPC ............. *A61F 2/2409* (2013.01); *A61F 2/2418* (2013.01); *A61L 27/04* (2013.01); *A61L 27/34* (2013.01); *A61F 2210/0014* (2013.01); *A61F 2210/0076* (2013.01); *A61F 2220/0016* (2013.01); *A61F 2230/0065* (2013.01); *A61F 2230/0078* (2013.01); *A61F 2250/007* (2013.01); *A61F 2250/0069* (2013.01); *A61L 2430/20* (2013.01)

(58) Field of Classification Search
CPC ....... A61F 2/24; A61F 2/2409; A61F 2/2418; A61F 2250/0069; A61F 2250/007
See application file for complete search history.

(56) References Cited

U.S. PATENT DOCUMENTS

| 2007/0005129 A1 | 1/2007 | Dam et al. |
| 2009/0125098 A1 | 5/2009 | Chuter |

(Continued)

FOREIGN PATENT DOCUMENTS

| CA | 2 752 660 | 8/2010 |
| EP | 1 849 440 | 10/2007 |
| EP | 1 977 718 | 10/2008 |

(Continued)

*Primary Examiner* — David Isabella
*Assistant Examiner* — Suba Ganesan
(74) *Attorney, Agent, or Firm* — Clark & Brody

(57) ABSTRACT

The invention relates to an anchoring device (1, 100) for implanting a prosthetic heart valve at a valve annulus of a patient. According to the invention, such a device comprises: a compressible and expandable sealed ring member (2, 200); a compressible and expandable anchoring element (3, 300) having a ventricular skirt (33, 303) and an atrial skirt (31, 301) linked by a tubular portion (32, 302); said ring member (2, 200) surrounding said tubular portion (32, 302) of said anchoring element (3, 300) and said anchoring element clamping said prosthetic heart valve.

16 Claims, 6 Drawing Sheets

(56) References Cited

U.S. PATENT DOCUMENTS

2014/0214157 A1\* 7/2014 Bortlein et al. ............. 623/2.11
2014/0303719 A1\* 10/2014 Cox et al. .................... 623/2.11

FOREIGN PATENT DOCUMENTS

| WO | 2006/128185 | 11/2006 |
| WO | 2009/045338 | 4/2009 |

\* cited by examiner

ANCHORING DEVICE FOR A PROSTHETIC HEART VALVE

1. FIELD OF THE INVENTION

The field of the invention is that of designing and making medical devices for implanting in the human body.

More precisely, the invention relates to an anchor device for anchoring a prosthetic heart valve that is to be put into place by a doctor and/or a surgeon.

2. PRIOR ART

Heart valves are non-contractile elastic structures having the main purpose of allowing blood to flow through the organism in one direction only. More particularly, they prevent blood from flowing backwards in the heart or the arteries. There are four valves in the heart: the tricuspid valve, the pulmonary valve, the mitral valve, and the aortic valve. Each valve is attached to and surrounded by a respective valve annulus in the heart or in a vessel leaving the heart. Pathologies associated with malfunctions of these valves are designated by the term valve disease. The most common pathologies are as follows:
  stenosis: the valve does not open correctly;
  insufficiency or leakage: the valve closes poorly and blood flows backwards; and
  insufficiency and stenosis in combination.

Because of poor blood circulation in the organism, these pathologies generally lead to the patient being very tired, quickly becoming short of breath, edema of the lower limbs, severe chest pain, etc. . . . . Such malfunctioning ends up exhausting the heart. In particular, since the ejection orifice is narrowed with stenosis, intracardiac pressure increases. The heart thus delivers extra force in order to eject blood. In the long term, valve disease therefore leads to heart failure.

It is estimated that 2% of the adult population suffers at present from valve disease. This percentage seems to be constantly increasing, in particular because the population is aging. Certain valve diseases can be acquired such as those associating with taking medication such as amphetamines. Other valve diseases are due to a congenital anomaly. Nevertheless, the great majority of these diseases are associated with age and to valves degenerating. The preferred treatment is to replace the valve, which requires very burdensome surgery involving the use of extracorporeal circulation on the patient. The surgeon must then sew a valve onto the decalcified valve annulus. Apart from the costs, the complications, and the risks associated with such an operation, that option is applied only to patients who are in physical condition that is good enough to enable them to recover from such surgery. Unfortunately, 20% to 30% of the patients involved present high operative risk and are rejected for surgery.

Another possibility is to use a catheter to insert a prosthetic heart valve. Such prostheses are described in particular in application EP 1 977 718 A. In practice, that type of valve is contained in a self-expanding prosthesis of circular section. It is compacted in the catheter and it deploys automatically at the valve annulus. That type of prosthesis thus enables a larger number of patients to be treated, avoiding the drawbacks of surgery, and without any need to suture the patient.

Nevertheless, those prostheses of circular section present numerous drawbacks. The valve annulus, in particular in the mitral or tricuspid positions, presents a section that is oval. Furthermore, it deforms a little in operation and also over time. The circular section of the prosthesis is thus not perfectly matched to anatomical reality for certain annuluses. Small leaks of blood can then occur, which means that the patient's physical condition is not fully restored. Another drawback is that the prosthesis may be dislodged from the annulus that surrounds it under the pressure exerted by the blood, and that can lead to the patient's death.

Devices have been proposed for anchoring prosthetic valves to a valve annulus. Reference may be made in particular to application CA 2 752 660 A1, which describes a device enabling a prosthetic valve to be anchored to the valve annulus of a patient. Also known is application US 2007/0005129 A1, which describes a circular device for anchoring prosthetic valves, the device having hooks that enable valves to be fastened in the aorta. Nevertheless, those devices also present a section that is circular, which means that they do not overcome problems of incompatibility between the circular section of the prostheses and the oval section of the annulus. Furthermore, they do not enable the diameter of the prosthesis to be adapted to variations in the diameter of the annulus. The phenomenon of leakage thus remains. Those devices cannot be used for valves in the mitral or tricuspid positions and large amounts of leakage exist in the aortic position.

3. OBJECTS OF THE INVENTION

A particular object of the invention is to mitigate those drawbacks of the prior art.

More precisely, an object of the invention, in at least one embodiment, is to provide a device that enables a prosthetic heat valve to be held to the valve annulus.

Another object of the invention, in at least one embodiment, is to devise a device that is capable of adapting the apparent diameter of the prosthesis to the anatomical conditions of the patient.

Another object of the invention, in at least one embodiment, is to propose a device that is sufficiently long-lasting to continue performing its mission throughout the lifetime of a patient.

The invention also seeks, in at least one embodiment, to propose such a device that is simple to design and fabricate.

4. SUMMARY OF THE INVENTION

These objects and others that appear below are achieved with the help of an anchor device for implanting a heart valve prosthesis at a patient's valve annulus.

According to the invention, such a device comprises:
  a leakproof toroidal element that is compressible and expandable; and
  an anchor element presenting a compressible and expandable mesh structure together with a ventricular collar and an auricular collar connected together by a tubular portion;

said toroidal element surrounding said tubular portion of said anchor element and said anchor element encircling said heart valve prosthesis.

Thus, the invention relies on an entirely original approach that consists in associating an anchor element with another deformable element that behaves as an adapter between the valve annulus and a prosthetic valve of circular section. The shape of this deformable element is that of an open torus, suitable for receiving the prosthetic valve in its hole. An open torus is defined by sweeping a circle presenting a "minor" diameter around an axis lying in its plane and not passing through its center. An open torus presents a hole in its center.

The toroidal element is expandable and compressible in a radial direction. It thus enables the diameter of the prosthesis to be adapted to the anatomical configuration of each patient.

Thus, problems of prosthetic valves leaking and shifting, or indeed of them being ejected out from the valve annulus, are eliminated.

Furthermore, because of its deformability, the toroidal element makes it possible to accommodate the deformations of the valve annulus associated with the operation of the valve and/or with tissue aging. This characteristic also makes it possible to mitigate the leakage phenomenon associated with poor matching of diameters between the prosthetic valve and the valve annulus.

The anchor element enables the prosthetic valve and the toroidal element to be fastened more securely in the heart cavity. Because of its collars that project on either side of the annulus, the anchor element is suitable for withstanding the pressure exerted by blood on the device as a whole and on the prosthetic valve in particular. Furthermore, the collars hold the toroidal element between them and they prevent it from moving in a longitudinal direction. The toroidal element and the prosthetic valve thus cannot shift out from the annulus. In the meaning of the invention, each collar presents an external diameter that is greater than or equal to the external diameter of the toroidal element. This characteristic enables the device to be anchored in particularly secure manner, and consequently enables valve prostheses to be held better on their implantation sites.

Finally, the device is slightly overdimensioned relative to the anatomical dimensions of the patient. This overdimensioning of the elements of the device make it possible in particular to hold it in place by the assembly constantly compressing the annulus.

The mesh structure enables the device surrounding the prosthesis to pass easily from a retracted position, necessary for putting the prosthesis into place, to a deployed position in which it is functional. This mesh structure also enables the prosthesis to be compressed in order to be inserted into the catheter and enable it to be put into position without having recourse to surgery.

Preferably, said toroidal element also presents a mesh structure covered in a film of polymer material. This covering may be used either on the internal face of the toroidal element, or on the external face of the mesh. The covering by means of a polymer material film serves to avoid blood passing through the mesh of the toroidal element between the wall of the annulus and the outer wall of the heart valve prosthesis. More precisely, when the toroidal element is covered on its internal face, the mesh is left apparent. When the toroidal element is covered on its external face, the mesh is hidden by the film of polymer material.

In an even more preferred embodiment, said polymer material is selected from: silicone, polytetrafluoroethylene (PTFE), polyurethane, polyamide, polyester, fluorinated resin, or by a combination of at least two of these materials. These materials present the advantage of being well tolerated by the patient's organism and of being particularly leakproof. This covering in a leakproof polymer material contributes to eliminating the problem of leakage between the valve annulus and the prosthetic valve. The device of the invention thus considerably improves the performance of present prosthetic valves.

In the meaning of the invention, the anchor device is never covered in any kind of polymer material. The material constituting the device is left bare, so heart tissue invaginates through the mesh constituting the anchor element, thereby constituting anfractuosities enabling the device to withstand contractions of the heart and blood pressure. This physiological and normal phenomenon of the device being colonized by heart tissue serves in particular to anchor the device more securely in the heart.

In an advantageous embodiment, said mesh structure is made at least of a metal material having shape memory or a polymer material having shape memory.

In a preferred embodiment, said metal material with shape memory is selected from: nickel, titanium, cobalt, etc. . . . and a combination of at least two of these metals. In an even more preferred embodiment, said metal material with shape memory is an alloy of nickel and of titanium.

These materials present the advantage of being well tolerated by the patient, of enabling the device to be compressed while they are cold, and of returning almost immediately to their shape as soon as they return to body temperature.

In an advantageous embodiment, said tubular portion of said anchor element presents a height h less than the minor diameter d of said toroidal element. These dimensions correspond to the device when it is deployed, while not being subjected to any mechanical stress, and in particular when it is not in place in a patient's heart. The height h is defined as being the height between the two collars of the anchor element.

This particular characteristic enables the anchor element to clip the toroidal element between its collars. Thus, the various elements constituting the device of the invention are held firmly relative to one another. The absence of slack between these elements contributes firstly to holding the prosthesis in the device and secondly to holding the device as a whole in the valve annulus.

Advantageously, said toroidal element presents, over at least a portion of its external periphery, a zone of weakness against radial compression when in situation.

The term "radial compression when in situation" is used to mean the compression that is observed when the device is implanted in a patient's heart. The zone of weakness is preferably situated in the middle zone of the toroidal element. The middle zone may be defined as being a zone that is spread equally on either side of the midplane defined by the major circle constituting the toroidal element. This zone of weakness serves to ensure that deformation of the toroidal element under stress from the valve annulus in operation is not uncontrolled. It is preferable for the toroidal element to deform in a direction that is radial relative to the longitudinal axis of the prosthetic valve for implanting, and not in a direction parallel to the longitudinal axis. This characteristic enables the device of the invention to adapt better to the anatomy of each patient, and also to the deformations of the annulus in operation and/or over time. This thus enables the device to avoid being ejected from the annulus in operation. This also provides an additional degree of flexibility to avoid impeding proper operation of the prosthetic valve by stiffening the valve annulus in superfluous manner. This zone of weakness preferably extends in the implantation situation over approximately 5 millimeters (mm) on either side of the midplane of the toroidal element. This zone must enable the toroidal element to deform radially by not more than 5 mm when in the implanted situation.

Preferably, said zone of weakness against radial compression when in situation comprises a discontinuity in the mesh constituting said mesh structure of said toroidal element and/or the use of materials of variable elasticity such as an alloy of nickel and of titanium.

Advantageously, said toroidal element presents, over at least a portion of the surface defining its hole, a zone of increased resistance to radial compression when in situation. Preferably, said zone of increased resistance lies in the middle zone of said toroidal element. The purpose of having this middle zone is to ensure that the forces and mechanical stresses to which the anchor element and in particular the toroidal element is subjected are not transmitted to the prosthetic valve. Thus, the operation of the prosthetic valve is not degraded. This characteristic also contributes to maintaining the valve within the device at the valve annulus. Limiting the radial forces that are exerted on the wall of the prosthesis prevents the prosthesis from shifting little by little and then being ejected from the annulus.

Said zone of resistance to radial compression preferably extends in the implantation situation over about 5 mm on either side of the midplane of the toroidal element, at its internal diameter.

In a variant, said zone of increased resistance to radial compression when in situation comprises a mesh that is denser than the remainder of the mesh constituting said mesh structure of said toroidal element.

In another variant, said zone of increased resistance to radial compression when in situation comprises a reinforcing band. In this embodiment, a band of polymer material situated at the internal diameter of the toroidal element, in other words surrounding the hole of the torus in which the prosthetic valve is inserted, serves to encircle the prosthesis and limit radial compression thereof.

In a variant, said auricular collar and said ventricular collar of said anchor element are symmetrical.

In another variant, said auricular collar and said ventricular collar of said anchor element are asymmetrical. In this variant, the ventricular collar may for example be extended so as to enable it to be pressed against the walls of the ventricle while it is being implanted. Since the contact area is larger, the device is anchored more securely. Depending on the anatomical location of the device and of the valve that is to be replaced, the collar should be shaped so as to avoid obstructing any orifice of a vein or an artery that opens out into or leads away from the heart.

The dimensions given above apply to the device when deployed, independently of any mechanical stress and while not in position in a patient's heart.

In an advantageous embodiment, said toroidal element presents an external diameter D2 lying in the range 30 mm to 70 mm. Depending on the age, the weight, and the size of the patient, the toroidal element may be designed to have a variety of dimensions. In particular, it is possible to design devices in which the toroidal element may present an external diameter D2 that is equal to 30 mm, 40 mm, 50 mm, 60 mm, or 70 mm.

Advantageously, each of said collars of said anchor element presents an external diameter D4 lying in the range 40 mm to 70 mm. For example, each of the collars may present an external diameter D4 of 40 mm, 50 mm, 60 mm, or 70 mm. These dimensions may also be selected as a function of the anatomical destination of the heart valve prosthesis for implanting, and on the size and the weight of the patient.

In the invention, the external diameter D4 of each of the auricular and ventricular collars is greater than or equal than the external diameter D2 of the toroidal element, and preferably.

In an advantageous embodiment, the device of the invention also includes stabilization hooks. The presence of these hooks serves in particular to attach the device more firmly in the valve annulus and more generally in heart tissue. These hooks are particularly useful when the device and the prosthesis have just been put into place. Colonization of the anchor device by heart tissue does not take place instantaneously. The hooks then enable the device of the invention to be anchored more securely for the time it takes tissue to develop around the anchor device.

In a preferred embodiment, at least some of said hooks are distributed on the external diameter D2 of said toroidal element. The presence of hooks at the circumference of the toroidal element enables it to be anchored in the valve annulus.

In a preferred variant, at least some of said stabilization hooks are provided on at least one of said auricular collar and said ventricular collar. The presence of these hooks serves in particular to fasten the device in heart tissue.

Said hooks are preferably distributed uniformly. A uniform distribution at the circumference of the toroidal element or over at least one of said collars of the anchor element serves to distribute the pulling forces that act both on the heart tissue and on elements of the device.

In even more preferred manner, the hooks may be distributed at an angle lying in the range 5° to 30°, and preferably at an angle of 15°, over the external circumference of the toroidal element and/or over the external diameter of at least one of said auricular and ventricular collars.

In a particular advantageous embodiment, when stabilization hooks are provided on the toroidal element, said stabilization hooks are distributed uniformly both on the midplane of said toroidal element and also on either side of said midplane.

Advantageously, said stabilization hooks have a length lying in the range 1 mm to 3 mm, and a thickness lying in the range 0.1 mm to 1 mm. Said stabilization hooks preferably have a length of 3 mm and a thickness of 1 mm.

5. LIST OF FIGURES

Other characteristics and advantages of the invention appear more clearly on reading the following description of preferred embodiments of the anchor device for a prosthetic heart valve, given merely as illustrative and non-limiting examples, and with reference to the accompanying drawings, in which.

6. DESCRIPTION OF AN EMBODIMENT OF THE INVENTION

The general principle of the invention lies in the design of a device enabling a prosthetic valve to be anchored within a valve annulus, said device also behaving as an adapter between the circular section of such a prosthesis and the generally oval section of the valve annulus of a patient. Such a device thus comprises a toroidal element in the form of an open torus. The prosthetic valve is housed in the hole in this element. The toroidal element is compressible and expandable in a radial direction. This characteristic enables the element to deform to adapt to the anatomy of the patient. It can also adapt when the valve annulus deforms, either while it is in operation, or else over time. The toroidal element cooperates with an anchor element that serves to implant the device in heart tissue. Co-operation between these elements serves to hold the prosthetic valve in place in the valve annulus. This serves to avoid the problems of blood leaking from one cavity to another that stems from present-day prosthetic valves not fitting well enough to the anatomical reality of the valve annulus. The problem of the prosthetic valve shifting or even being ejected from the valve annulus is thus eliminated.

6.1 Fabricating Prostheses of the Invention

Prostheses of the invention are fabricated by any method well known to the person skilled in the art. The method of fabricating such prostheses does not constitute the subject matter of the present application.

Specifically, such prostheses may be fabricated from a metal wire of shape memory material so as to form two tubular mesh elements. For example, the metal wire of shape memory material is twisted manually on a former to form a tubular element of gridded structure. The tubular element may be cut to the appropriate dimensions either manually or by laser in order to obtain clean cuts at the ends of the wire. One of the tubular elements is then shaped to form the anchor element and the other of these tubular elements is subsequently shaped to form the toroidal element. Shaping may be performed by applying a high temperature in localized manner while simultaneously exerting mechanical stress on the tubular element in order to be able to change its curvature. The temperature that is to be applied needs to be sufficiently high to cause the material to deform but without leading to the metal material of the wire melting. This temperature depends on the nature of the material, on the qualitative and quantitative composition of the metal alloy, . . . .

An embodiment of the invention is described below with reference to FIGS. 1 to 5. The elements making up the device are shown in FIGS. 1 to 5 in their expanded states while free of any mechanical stress.

6.2 An Embodiment of the Toroidal Element of the Invention

Figure 1:
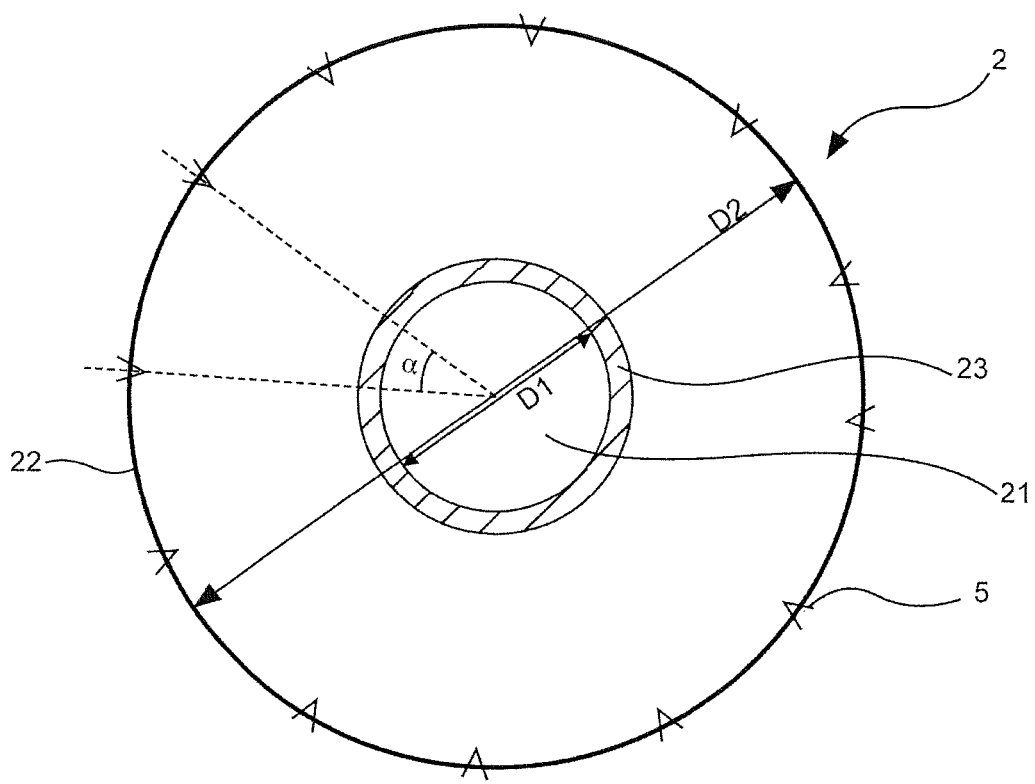
FIG. 1 is a diagrammatic plan view of a toroidal element in a first embodiment shown in its deployed state.

FIG. 1 is a plan view of the toroidal element 2. This element is in the form of an open torus, i.e. a torus that has a central hole.

Mathematically, a torus is generated by sweeping a minor circle around an axis. The diameter of the circle is referred to as the minor diameter.

The toroidal element shown in FIG. 1 possesses an internal diameter D1 corresponding to the diameter of the hole 21 in the torus, and an external diameter D2. The diameter D2 may lie in the range 40 mm to 70 mm, depending on the anatomical destination and on the patient to be treated. The height of the torus is equal to the minor diameter d of the minor circle. The internal diameter D1 is compressible. The diameters D1 and D2 are shown in FIG. 1 as being slightly offset for greater readability.

Advantageously, the toroidal element may be covered entirely in a leakproof polymer material 22 such as polytetrafluoroethylene (PTFE). This covering enables the toroidal element to be completely leaktight, thus making it possible to solve completely the problem of valve leakage and regurgitation.

The element 2 also has a reinforcing band 23, this and also being made of PTFE. The reinforcing band 23 surrounds the hole 21 and serves to limit radial deformation in the middle zone. This reinforcing band serves to prevent the diameter D1 exceeding 30 mm in its middle zone while the device is being implanted.

Figure 2:
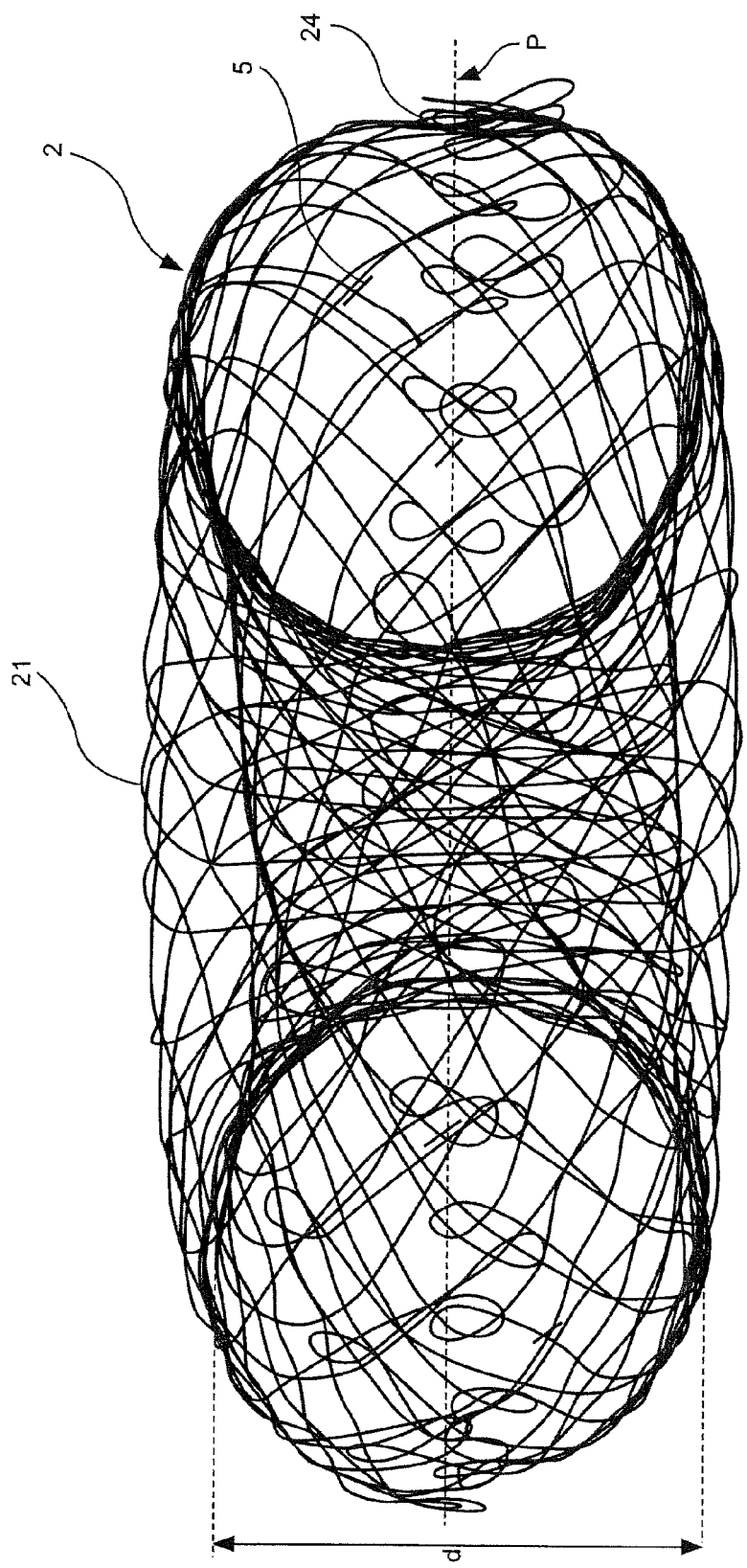
FIG. 2 is a side view of the toroidal element in its deployed state.

In this embodiment, the element 2 has stabilization hooks 5 enabling the element 2 to be anchored in heart tissue, and more precisely in the valve annulus of a patient's heart. These hooks 5 are placed on the external circumference of the toroidal element 2. They present a length of 3 mm, a thickness of less than 1 mm, and they are made out of the same material as the device 1. The hooks are distributed uniformly at an angle alpha ($\alpha$) lying in the range 5° to 30°, preferably at an angle of 15°. The hooks may also be uniformly distributed on either side of the midplane P of the torus, as shown in FIG. 2 (using a dashed line). In this figure, one-third of all of the hooks lie under the midplane P, at about 3 mm from the midplane, one-third lie on the midplane P, and the remaining third of the hooks lie above the midplane P, likewise at about 3 mm. The hooks situated above and below the midplane P are equidistant from the line of the plane. The fact that the hooks are uniformly distributed over the entire circumference and on either side of the midplane P enables the toroidal element 2 to be anchored more securely to the valve annulus of the patient.

At its external diameter D2, the toroidal element 2 has a zone 24 of weakness against radial compression. In this embodiment, this zone may be obtained by discontinuity in the mesh or by using a material of varying modulus of elasticity, such as an alloy of nickel or titanium. This discontinuity may be obtained when making the toroidal element by shaping a mesh tubular element so that its ends are looped externally one towards the other. This zone of weakness enables the element 2 to deform preferentially at its external diameter D2, thereby contributing initially to making the device 1 easier to insert. This zone also enables the toroidal element 2 to adapt more easily to the anatomy of the valve annulus. Furthermore, when the annulus deforms during opening or closing of the valve, the presence of the zone 24 enables the element to deform in a direction that is radial and not longitudinal relative to the axis of the prosthesis. This feature contributes to holding the element in the annulus. If the element 2 were to deform in uncontrolled manner, it would run the risk of being more easily shifted out from the annulus. Radial compression should preferably be made easy in order to accommodate variation of about 5 mm. Compression should be difficult beyond that value. Otherwise, the toroidal element would be too deformable and would not perform correctly its adapter function between the valve annulus and the prosthetic valve.

6.3 Example of a First Embodiment of the Anchor Element of the Invention

Figure 3:
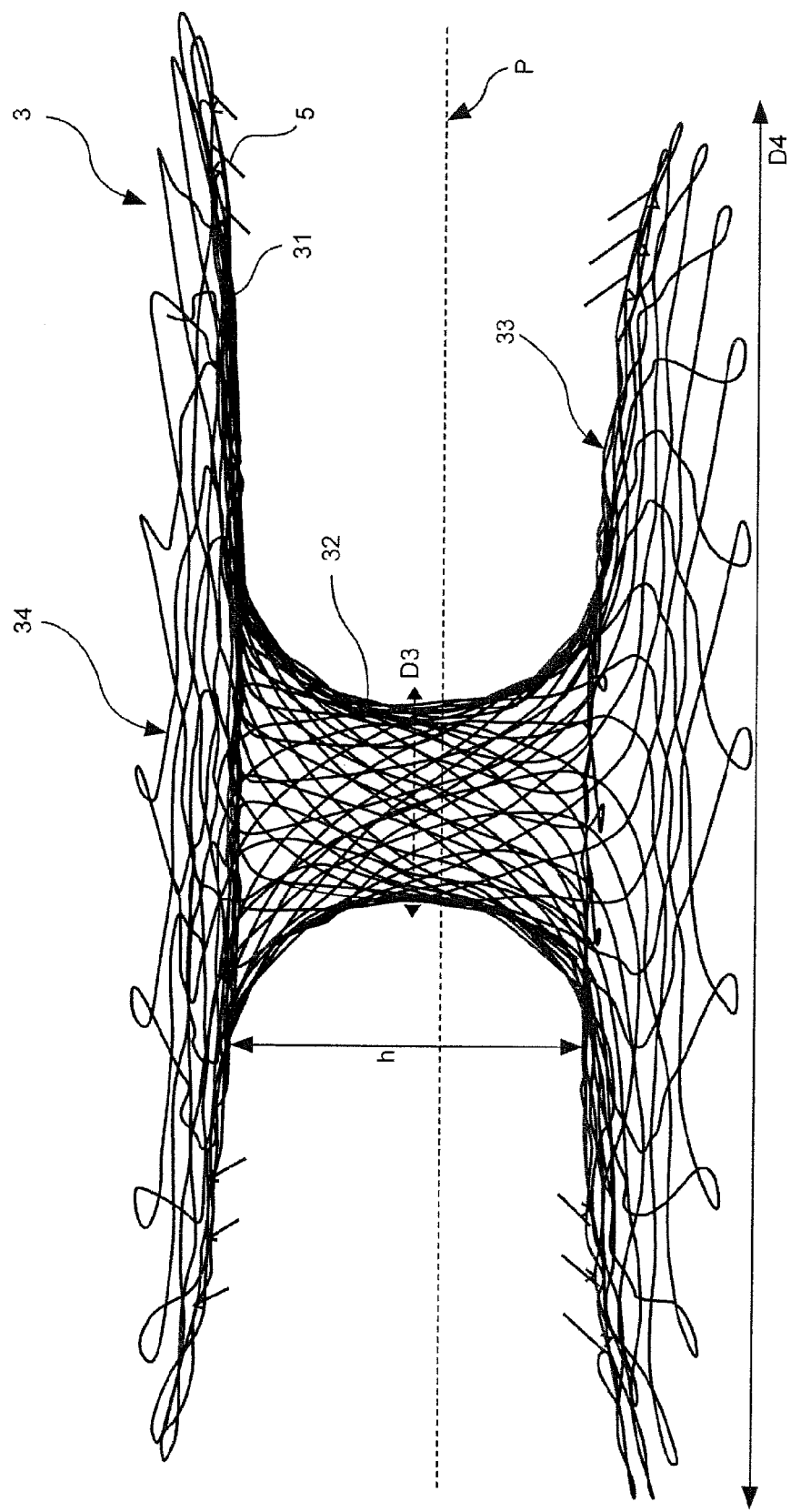
FIG. 3 is a side view of the anchor element of the invention in its deployed state.

FIG. 3 is a cross-section of the anchor element 3. This element presents two collars 31 and 33 that are spaced apart by a tubular portion 32 of height h. In this embodiment, the auricular and ventricular collars 31 to 33 are symmetrical. They present a diameter D4 which may lie in the range 40 mm to 70 mm. The tubular portion presents a diameter D3, which is measured in the midplane P of the anchor element 3, and which is equal to 10 mm. In the invention, the anchor element is preferably not covered in any polymer material.

The lumen 34 of this portion 32 serves to receive a prosthetic valve. The anchor element 3 is inserted in the opening 21 of the torus so that the toroidal element surrounds the tubular portion 32. The height h of the anchor element 3 is slightly smaller than the diameter d of the minor circle of the toroidal element 2. This characteristic results in the toroidal element 2 being slightly flattened between the collars 31 and 33. This serves to prevent there being too much slack between the element 2 and the anchor element 3. These elements thus co-operate closely. The prosthetic valve is thus held better by the device of the invention. The auricular and ventricular collars 31 and 33 present stabilization hooks 5 on their surfaces that come into contact with the heart walls. These hooks are identical to those described above: they are 3 mm long, about 0.1 mm to 1 mm thick, and they are distributed uniformly over the surfaces of the collars at an angle $\alpha$ of about 15°. The hooks point towards the tubular portion 32 and form an angle of about 90° with the surfaces of the collars.

6.4 Example of a First Embodiment of the Assembled Device of the Invention

Figure 4:
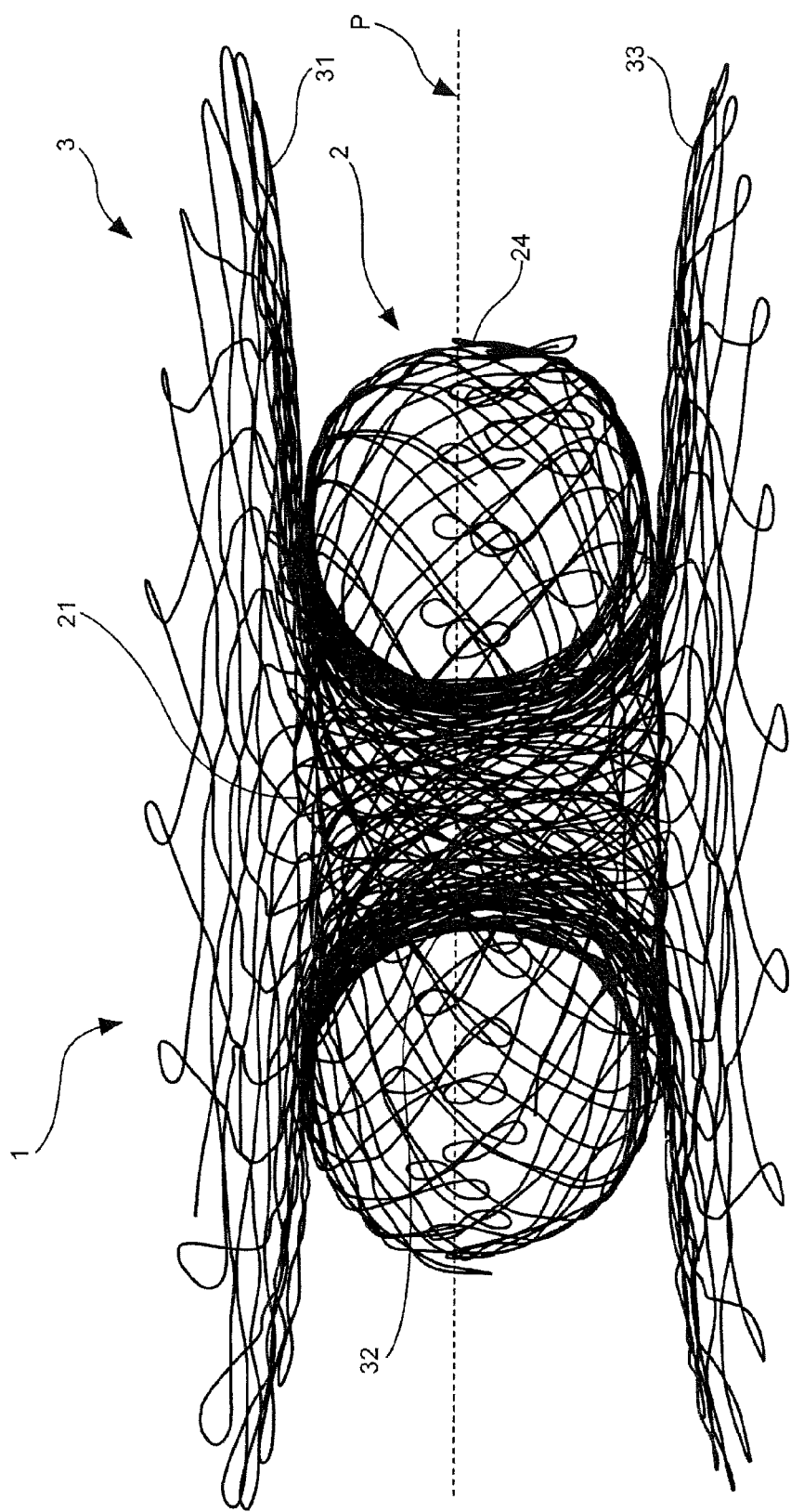
FIG. 4 is a side view of the assembled device in this first embodiment, in its deployed state.
Figure 5:
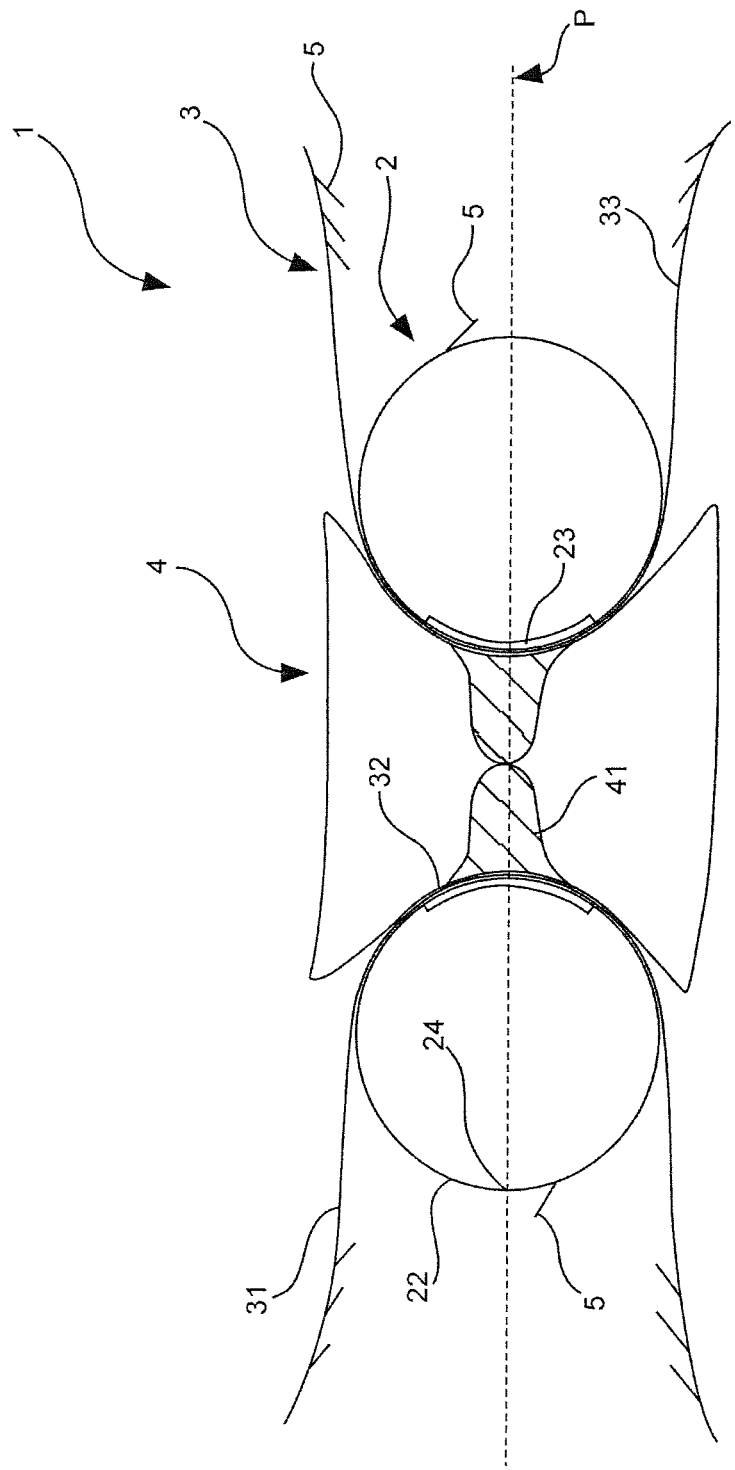
FIG. 5 is a side view of the assembled device in this first embodiment shown housing a prosthetic valve.

A first example of the anchor device of the invention is described with reference to FIGS. 4 and 5. FIG. 4 is a photograph of the assembled device 1 in side view. FIG. 5 is a side view of the assembled device while housing a prosthetic valve.

The device 1 comprises an anchor 3 and a toroidal element 2. The toroidal element is identical to that described in FIGS. 1 and 2 and forms an open torus, thus having a hole 21. Its external diameter D2 is about 50 mm and its internal diameter D1 is equal to 10 mm. The diameter of its minor circle is 21.5 mm. The toroidal element 2 is covered in a leakproof polymer film 22 of polytetrafluoroethylene (PTFE). This film is not shown in FIG. 4, in order to reveal the structure of the element 2. At its internal diameter D1, the element 2 is provided with a reinforcing band 23 of PTFE. This band, which measures 10 mm, extends in the midplane P and over the internal face of the toroidal element 2. More precisely, this reinforcing band 23 extends over 5 mm on either side of the midplane P. The midplane P is shown as a dotted line in FIGS. 4 and 5. The toroidal element also has a zone of weakness 24 in its external diameter D2, constituted by a discontinuity in the meshing, as shown in FIG. 4.

The anchor element 3 has two collars, an auricular collar 31 and a ventricular collar 33 that are separated by a tubular portion 32. Its external diameter D4 is about 70 mm and the internal diameter D3 is equal to the diameter D1, i.e. 10 mm. The height h of the tubular portion 32 is 20.5 mm, and is thus slightly less than the height of the toroidal element 2. In this example the ratio D4/D2 is 1.4. The tubular portion 32 is inserted in the hole 21 of the toroidal element so that the element 2 surrounds the tubular portion 32. This combination of characteristics enables the elements 2 and 3 to co-operate closely, thereby enabling the valve to be held firmly in the core of the device, avoiding involuntary shifting of the elements relative to each other and coordinating deformations of the device as a function of deformations of the annulus and as a function of opening of the valve.

The tubular portion 32 and the hole 21 together define a housing suitable for receiving a prosthetic heart valve 4 that may have two or three flaps or "leaflets" 41. The prosthetic valve is in the form of a tube having a diameter of about 40 mm in its expanded and unstressed state. Its radial expansion is limited by compression from the device 1 so that it is held firmly inside the device 1.

The toroidal element 2, the anchor element 3, and the prosthetic valve 4 are expandable and compressible in a radial direction. This characteristics enables the assembly to be compressed in order to enable it to be inserted in the catheter that is used for placing the assembly in the heart, without needing to open the patient's rib cage. This characteristic also enables the device 1 and the prosthesis 4 to recover their shapes, after the catheter has been withdrawn. Advantageously, the elements 2, 3, and 4 present a mesh structure. This structure is visible in FIG. 4, but it is not shown in FIG. 5 for reasons of clarity. The mesh structure may be made using a metal material having shape memory, preferably an alloy of nickel and of titanium. This type of material, and in particular the alloy of nickel and of titanium, presents the feature of being easily compressible when cold, thereby facilitating insertion into the catheter. They are also capable of recovering their shape instantaneously at a higher temperature, and in particular at body temperature.

In this embodiment, the ventricular and auricular collars 31 and 33 are provided with stabilization hooks 5 on their surfaces that come into contact with heart tissue. These hooks are identical to those described in FIG. 2. The toroidal element 2 is also provided with hooks 5 in the middle zone 24 of its external circumference. As described above, the hooks 5 are distributed of an angle α of 30° over the entire circumference of the element 2, in the midplane P and also on either side of the midplane P, as explained above. Furthermore, they form an open angle of about 30° with the wall of the toroidal element 2. The presence of these hooks serves in particular to fasten the device and the prosthetic valve more securely both to the valve annulus and in the heart cavity of the patient.

In a variant, it is possible to provide only the anchor device or only the toroidal element with such hooks. It is also possible to provide no hooks, with the shaping of the device sufficing to perform its function of adapting and anchoring the prosthetic valve.

Nevertheless, it is preferable for hooks to be present since they enable the device to be held securely during the time heart tissue is developing around the mesh of the anchor element.

Figure 6:
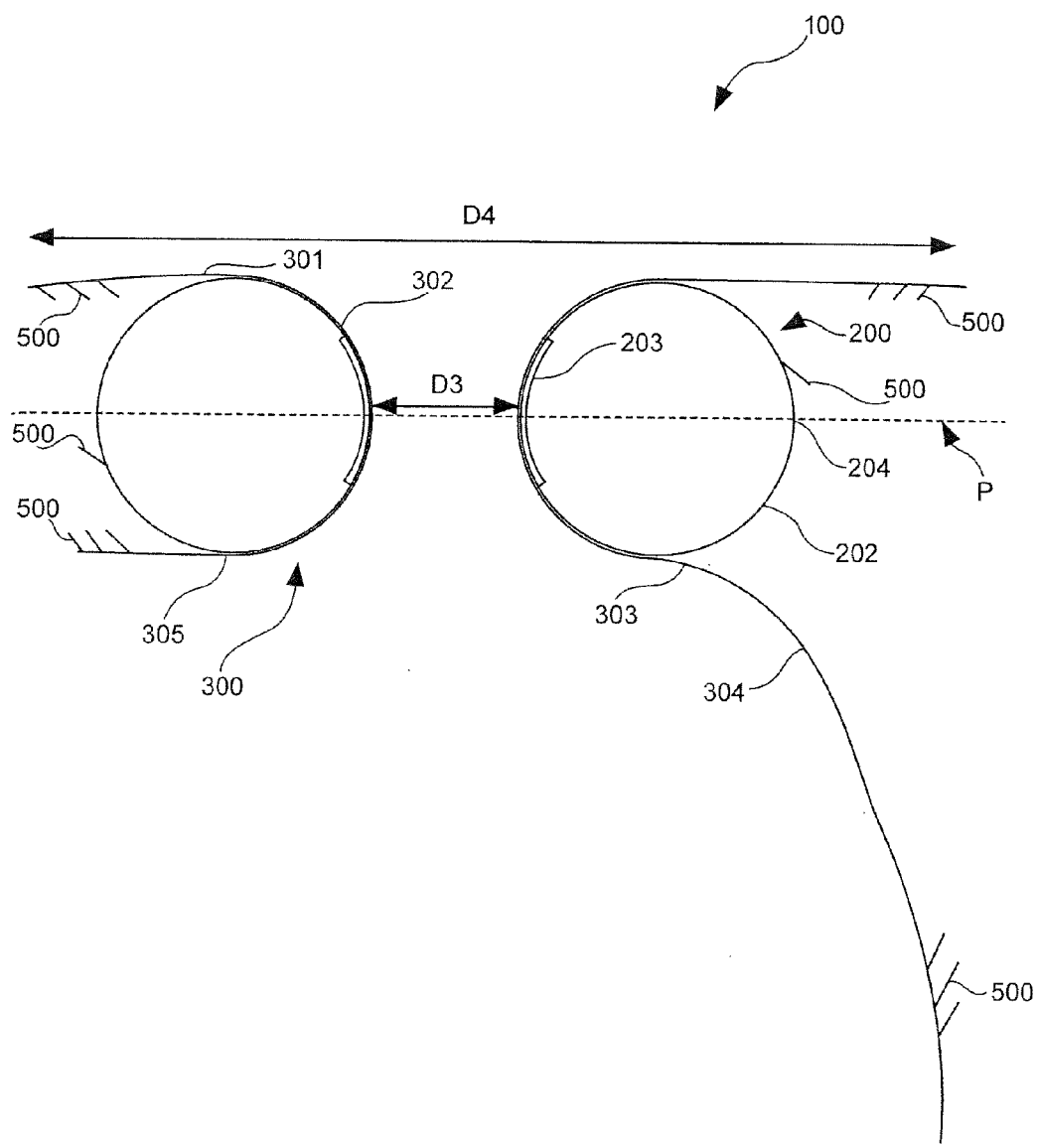
FIG. 6 is a diagrammatic side view of a second embodiment of the device of the invention.

6.5 Example of a Second Embodiment of an Assembled Device of the Invention Incorporating an Anchor Element with Asymmetrical Collars FIG. 6 is a side view of a second embodiment of the invention. The device 100 of the invention comprises a toroidal element 200 identical to that described at Points 6.2 and 6.4. This toroidal element 200 is also covered in a leakproof polymer film 202. It also presents a zone of weakness 204 and a reinforcing band 203 of PTFE, both situated in the midplane P of the toroidal element 200 (midplane shown as a dashed line). This reinforcing band is identical to the reinforcing band 23 of the first embodiment.

Nevertheless, the anchor element 300 differs from that described at Points 6.3 and 6.4. This anchor element 300 has two collars, an auricular collar 301 and a ventricular collar 303 that are spaced apart by a tubular portion 302. In this embodiment, the collars are asymmetrical, both in shape and in size on either side of the midplane P. The auricular collar 301 is generally circular in shape with an external diameter D4 that may lie in the range 50 mm to 70 mm. The tubular portion presents a diameter D3 of about 10 mm. In contrast, the ventricular collar is asymmetrical in shape. It has a longer portion 304 and a shorter portion 305. The portion 304 is for extending along the internal wall of the ventricle, while the shorter portion 305 extends in the portion under the annulus. This asymmetrical shape enables the device of the invention to be anchored more securely in the heart since the contact area with tissue is greater. In contrast, the shorter portion 305 makes it possible to avoid closing the aortic orifice, for example, in the event of the valve of the invention being for anchoring a prosthetic valve that replaces the mitral valve.

The elements 200 and 300 also have stabilization hooks 500. These hooks 500 are distributed on the toroidal element and on auricular collar as explained above. Briefly, the hooks 500 are distributed on the external circumference of the toroidal element 200. They are distributed both in the midplane P of the element 200 and also on either side of the midplane P, at an angle of 30°. Hooks are also provided on the auricular collar at an angle alpha of 30°. They point towards the tubular portion 302 of the element 300 and form an angle of 30° relative to the surface of the collar.

In a variant, stabilization hooks 500 are also provided on the ventricular collar 303. These hooks 500 are uniformly distributed at an angle of 30° and they form an angle of 30° with the surface of the collar. In another variant, it is also possible to provide additional stabilization hooks in the long portion 304 in order to reinforce the anchoring of the device 100 in heart tissue.

The invention claimed is:

1. An anchor device (1, 100) configured to cooperate with a heart valve prosthesis to be implanted at a patient's valve annulus, said device comprising:
 a leakproof toroidal element (2, 200) that is compressible and expandable, comprising an external periphery and a surface defining a hole; and
 an anchor element (3, 300) presenting a compressible and expandable mesh structure comprising a ventricular collar (33, 303) and an auricular collar (31, 301) connected together by a tubular portion (32, 302);
 said toroidal element (2, 200) surrounding said tubular portion (32, 302) of said anchor element (3, 300) and said anchor element being intended to encircle said heart valve prosthesis;
 wherein said toroidal element (2, 200) presents, over at least a portion of its external periphery, a zone of weakness (24, 204) against radial compression when in situation and said toroidal element (2, 200) presents, over at least a portion of the surface defining its hole, a zone (23, 203) of increased resistance to radial compression when in situation.

2. A device according to claim 1, characterized in that said toroidal element (2, 200) presents a mesh structure covered in a film (22, 202) of polymer material.

3. A device according to claim 2, characterized in that said polymer material is selected from: silicone, polytetrafluoroethylene (PTFE), polyurethane, polyamide, polyester, fluorinated resin, or by a combination of at least two of these materials.

4. A device according to claim 2, wherein the zone of weakness is obtained by using a material of varying modulus of elasticity.

5. A device according to claim 1, characterized in that said mesh structure is made at least of a metal material having shape memory or a polymer material having shape memory.

6. A device according to claim 1, characterized in that said tubular portion (32, 302) of said anchor element (3, 300) presents a height h and said toroidal element presents a minor diameter d, wherein the anchor element height h is less than the minor diameter d of said toroidal element (2, 200).

7. A device according to claim 1, characterized in that said zone of weakness (24, 204) against radial compression when in situation comprises a discontinuity in the mesh constituting said mesh structure of said toroidal element (2, 200).

8. A device according to claim 1, characterized in that said zone (23, 203) of increased resistance to radial compression when in situation comprises a mesh that is denser than the remainder of the mesh constituting said mesh structure of said toroidal element (2, 200).

9. A device according to claim 1, characterized in that said zone of increased resistance to radial compression when in situation comprises a reinforcing band (23, 203).

10. A device according to claim 1, characterized in that said auricular collar (31) and said ventricular collar (33) of said anchor element (3) are symmetrical.

11. A device according to claim 1, characterized in that said auricular collar (301) and said ventricular collar (303) of said anchor element (300) are asymmetrical.

12. A device according to claim 1, characterized in that said toroidal element (2, 200) presents an external diameter D2 lying in the range 30 mm to 70 mm.

13. A device according to claim 1, characterized in that each of said collars (31, 33, 301, 303) of said anchor element (3, 300) presents an external diameter D4 lying in the range 40 mm to 70 mm.

14. A device according to claim 1, characterized in that it further includes stabilization hooks (5, 500).

15. A device according to claim 14, characterized in that at least some of said hooks (5, 500) are distributed on the external diameter D2 of said toroidal element (2, 200).

16. A device according to claim 14, characterized in that at least some of said stabilization hooks (5, 500) are provided on at least one of said auricular collar (31, 301) and said ventricular collar (33, 303).

* * * * *